(12) United States Patent
Danze et al.

(10) Patent No.: US 11,564,791 B2
(45) Date of Patent: Jan. 31, 2023

(54) DEVICE TO BE IMPLANTED IN A SUBJECT'S BODY TO FORM AN IMPLANT, AND ASSOCIATED TISSUE MASS AND METHOD

(71) Applicants: CENTRE HOSPITALIER REGIONAL UNIVERSITAIRE DE LILLE, Lille (FR); UNIVERSITE DE LILLE, Lille (FR); Julien Payen, Fournes en Weppes (FR)

(72) Inventors: Pierre-Marie Danze, Lille (FR); Philippe Marchetti, Lille (FR); Pierre Guerreschi, Lille (FR); Julien Payen, Lille (FR)

(73) Assignees: CENTRE HOSPITALIER REGIONAL UNIVERSITAIRE DE LILLE; UNIVERSITE DE LILLE; Julien Payen

( * ) Notice: Subject to any disclaimer, the term of this patent is extended or adjusted under 35 U.S.C. 154(b) by 119 days.

(21) Appl. No.: 16/340,240

(22) PCT Filed: Oct. 18, 2017

(86) PCT No.: PCT/IB2017/056464
§ 371 (c)(1),
(2) Date: Apr. 8, 2019

(87) PCT Pub. No.: WO2018/078489
PCT Pub. Date: May 3, 2018

(65) Prior Publication Data
US 2020/0222175 A1    Jul. 16, 2020

(30) Foreign Application Priority Data
Oct. 28, 2016   (FR) .................... 16/70642

(51) Int. Cl.
*A61F 2/12* (2006.01)
*A61F 2/00* (2006.01)

(52) U.S. Cl.
CPC .............. *A61F 2/12* (2013.01); *A61F 2/0077* (2013.01); *A61F 2210/0004* (2013.01); *A61F 2240/002* (2013.01)

(58) Field of Classification Search
CPC .. A61F 2/12; A61F 2/52; A61F 2/0077; A61F 2/0063; A61F 2210/0004; A61F 2240/002; A41C 3/10
See application file for complete search history.

(56) References Cited

U.S. PATENT DOCUMENTS

| 5,545,217 A | 8/1996 | Offray et al. ............ 623/8 |
| 6,432,138 B1 * | 8/2002 | Offray ............ A61F 2/12 623/8 |

(Continued)

FOREIGN PATENT DOCUMENTS

| WO | WO 01/66039 A1 | 9/2001 | |
| WO | WO-0166039 A1 * | 9/2001 | ............ A61F 2/12 |
| WO | WO 2012/122215 A2 | 9/2012 | |

OTHER PUBLICATIONS

Ogulata, T, "Air Permeability of Woven Fabrics"; Journal of Textile and Apparel, Technology and Management (2006) 5(2):1-10 (Year: 2006).*

(Continued)

*Primary Examiner* — Jennifer Dieterle
*Assistant Examiner* — Rebecca Lynee Zimmerman
(74) *Attorney, Agent, or Firm* — Ostrolenk Faber LLP

(57) ABSTRACT

A device to be implanted in a subject's body to form an implant for replacing and/or increasing a volume of soft tissue, the device being of the type including a three-dimensional frame which defines an inner space in the frame. The frame is typically bio-absorbable and includes (Continued)

two side apertures forming a transverse passage for inserting a vascular pedicle. The device further has at least two bio-absorbable textile sheets that can be stacked on each other in the inner space of the frame.

13 Claims, 8 Drawing Sheets

(56) References Cited

U.S. PATENT DOCUMENTS

| | | | | |
|---|---|---|---|---|
| 2004/0052768 A1* | 3/2004 | Morrison | ............... | A61K 35/12 |
| | | | | 424/93.7 |
| 2007/0104695 A1* | 5/2007 | Quijano | ............. | A61L 27/3804 |
| | | | | 424/93.7 |
| 2011/0144763 A1* | 6/2011 | Bagga | ..................... | A61L 27/10 |
| | | | | 623/23.61 |
| 2013/0253646 A1 | 9/2013 | Altman et al. | ..................... | 623/8 |
| 2014/0081296 A1* | 3/2014 | Palmer | ................. | A61F 2/0063 |
| | | | | 606/151 |
| 2014/0135925 A1 | 5/2014 | Brooks et al. | ..................... | 623/8 |
| 2014/0141050 A1* | 5/2014 | Ploger | ..................... | A61L 15/22 |
| | | | | 424/402 |
| 2019/0048521 A1* | 2/2019 | Meemaduma | ........ | B29C 51/262 |

OTHER PUBLICATIONS

International Search Report dated Mar. 21, 2018 in corresponding PCT International Application No. PCT/IB2017/056464.

Written Opinion dated Mar. 21, 2018 in corresponding PCT International Application No. PCT/IB2017/056464.

M.W. Findlay et al., "Tissue-Engineered Breast Reconstruction: Bridging the Gap toward Large-Volume Tissue Engineering in Humans," Plastic and Reconstructive Surgery, vol. 128, No. 6, pp. 1206-1215 (2011).

W.A. Morrison et al., "Creation of a Large Adipose Tissue Construct in Humans Using a Tissue-engineering Chamber: A Step Forward in the Clinical Application of Soft Tissue Engineering," EbioMedicine, vol. 6, pp. 238-245 (2016).

* cited by examiner

A

B

DEVICE TO BE IMPLANTED IN A SUBJECT'S BODY TO FORM AN IMPLANT, AND ASSOCIATED TISSUE MASS AND METHOD

CROSS-REFERENCE TO RELATED APPLICATIONS

The present application is a 35 U.S.C. §§ 371 national phase conversion of PCT/IB2017/056464, filed Oct. 18, 2017, which claims priority to French Patent Application No. 16/70642, filed Oct. 28, 2016, the contents of which are incorporated herein by reference. The PCT International Application was published in the French language.

TECHNICAL FIELD

The present invention concerns a device adapted to be implanted in the body of a subject to form an implant capable of replacing and/or increasing a soft tissue volume, a tissue mass and a method for manufacturing said implant.

PRIOR ART

Breast implants comprising a pocket filled with silicone gel are commonly used. Nevertheless, there are risks of break-up of the pocket which are not negligible. Hence, we have looked for alternatives to these breast implants.

Thus, the document WO 01/66039 A1 describes a porous shell which comprises several textile layers in the inner volume defined thereby. The shell is designed so that, after implantation in the body of a patient, it is filled up with liquid and contains little tissue or cells. Thus, we obtain a prosthesis which forms a liquid pocket, the liquid being produced by the organism of the patient. This shell does not enable the introduction of a pedicle.

The document U.S. Pat. No. 5,545,217 A1 describes a textile shell which comprises a mass of fibers that do not form a textile. After implantation, the shell is filled up with fluid and it is hoped that tissues will develop therein. Thus, we obtain a shell filled with tissues and biological fluid generated by the organism of the treated patient.

The article «Tissue-engineered Breast Reconstruction: Bridging the Gap toward Large-Volume Tissue Engineering in Humans» (M. W. Findlay et Al) published in 2011 in the journal PRSJournal (volume 128, issue 6, pages 1206 to 1215), describes a polycarbonate shell which comprises a bottom and a cambered portion both of which are perforated. The shell comprises a poly(L-lactide-co-glycolide) sponge which occupies half the inner volume of the shell. This shell is used for breast reconstruction in a technique which uses a derivative vascular pedicle and an adipose tissue. The pedicle is inserted into the shell, the adipose tissue is disposed on the latter. The pedicle should enable the vascularization and therefore the feeding of the adipose tissue which should grow and fill the shell. Thus, we obtain a fatty tissue volume which is formed in situ in the body of the patient. The results indicate that the sponge hinders the proliferation of the cells of the adipose tissue and ultimately no vascularization of the latter could be obtained.

In order to attempt to remedy to this problem, the document US 2014/0135925 A1 proposes a breast implant which comprises a shell made into two portions. The shell comprises a flat bottom which is equipped with perpendicular fins at the bottom and a cambered portion which comprises inner partition walls parallel to each other. When the shell is formed by assembly of the bottom and of the cambered portion, we obtain a partitioned space which enables the deposition of a layer of vascularized adipose tissue which thus fills the entire shell. The shell comprises two openings for the passage of a pedicle intended to feed the adipose tissue housed in the shell. This type of shell is difficult to make and the deposition of the tissue in the latter is not easy.

Similarly, the document US 2014/135925 A1 describes all techniques that can be used for the set-up of a breast prosthesis. The prosthesis described in this document includes a shell which enables the insertion of a vascular bed inside the shell, this bed filling, as of the set-up of the shell, the entire volume of the latter. The shell includes one single opening for the insertion of the vascular bed, which zigzags in the shell, supported by transverse inner fins. The shell is bioresorbable. This shell does not include any textile or openings for the passage of a pedicle through the shell.

The article entitled «Creation of a Large Adipose Tissue Construct in Humans Using a Tissue-engineering Chamber: A Step Forward in the Clinical Application of Soft Tissue Engineering» (W. A. Morrison et Al.) published in the journal EbioMedecine in April 2016 describes the use of an acrylic and perforated shell or chamber, for the surgical technique previously described for breast reconstruction. The bottomless shell is deposited on a fatty scrap comprising a vascular pedicle at the level of the location of the breast of the patient having undergone a mastectomy. The wound is closed and we observe the development of the fatty tissue. The latter develops and vascularizes only in some patients, but remains unable to fill the chamber. A case of capsular contraction is also recorded. Moreover, the shell is not resorbable and a second surgical act is necessary to remove it.

An object of the present invention is to provide a new device adapted to be implanted in the body of a subject in order to replace and/or increase a soft tissue volume.

Another object of the present invention is to provide a new device adapted to be implanted in the body of a subject which enables the growth of cells capable of forming a soft tissue, this new soft tissue formed in situ in the body allows replacing and/or increasing a soft tissue volume of the body of the subject.

The present invention concerns a device adapted to be implanted in the body of a subject to form an implant capable of replacing and/or increasing a soft tissue volume, said device being of the type comprising a three-dimensional wireframe which defines a space internal to said wireframe. According to the invention, in a characteristic manner, said wireframe is bioresorbable, it comprises two lateral openings forming a transverse passage enabling the insertion of a vascular pedicle and the device further comprises at least two sheets of a bioresorbable tissue adapted to be stacked one on top of the other in said space internal to said wireframe.

Indeed, the inventors have set out that the presence of the sheets allows obtaining a homogeneous and compact tissue mass which may be easily inserted into the wireframe, possibly carved according to the desired shape and/or incised, in particular in order to insert a vascular pedicle therein. In addition, the tissue mass may develop in situ in the body of the subject so as to fill the wireframe, the volume that remains to be filled being smaller than if the wireframe was empty.

Moreover, the rigid wireframe forms a volume which delimits the growth of adipocytes and which creates a cellular growth chamber.

Preferably, the sheets have a shape adapted to the section of the wireframe according to which they are stacked. The sheets may be disposed parallel to the bottom (possibly open) of the wireframe or perpendicular to the latter.

The wireframe is not limited to that according to the invention; it may comprise a bottom which is removable or not, and which cooperates with the edge of the wireframe or the ends of the arches defined later on, so as to close the latter.

According to a first embodiment, the wireframe includes a wall which defines an edge and a plurality of perforations distributed over said wall and/or an open portion formed in said wall and extending above said edge of said wireframe, said open portion extending from the apex of the dome when said wireframe is substantially dome-like shaped. The presence of perforations or of the open portion promotes the growth in situ—in the body of the subject—of the cells of the stacking housed in the wireframe, as explained later on.

According to a variant which may be combined with the aforementioned embodiment, said wall further comprises two lateral openings forming a transverse passage at the level of said edge of said wireframe and/or above said edge.

For example, the lateral openings may consist of indentations which extend from the edge of the wireframe and over part of its height. Such openings allow easily adjusting the height positioning of the pedicle during the set-up of the device of the invention in the body of the subject. Thus, it is possible to insert the pedicle into the stacking of sheets, the pedicle being supported by one or several sheet(s) and also covered by one or several sheet(s). Such an arrangement promotes the vascularization of the tissue mass formed in situ.

The wireframe may also include assembled arches whose free ends are located in the same plane. The arches may be assembled according to one of their ends or along their length. This type of wireframe allows obtaining adapted shapes, for example, in the case of a breast implant.

The use of arches allows reducing the amount of material forming the wireframe. The latter is light, has a larger surface in contact with the body of the subject when it is implanted in the body of the subject and is therefore easily resorbable by the latter. It may also be easily produced, for example, by 3D printing.

Thus, the wireframe may include a first group of outer arches and a second group of inner arches, located in the space defined by said outer arches, the free ends of said arches of said first and second groups being located in the same plane. Thus, we obtain a solid and rigid wireframe which allows holding the sheets properly in place.

Preferably, said textile is formed by an interweaving of at least two threads, said textile forms a three-dimensional structure which includes at least two superimposed surface layers, forming the opposite two faces of said textile, said threads connect said surface layers, said interwoven threads form pores which pass throughout the thickness of said textile and said textile preferably includes connection points between said threads.

Preferably, the connection points are distributed so that said layers could be separated from each other in the direction of the thickness of the textile over at least 20%, preferably at least 30% and at least 50% of the surface of the textile. Connection points ensure the cohesion of the textile and are distributed so as to form in the textile some kind of pockets at the level of which the layers could be separated.

The inventors have set out that such a textile allows a good hooking of the cells and thus allows forming a mass which is compact and easy to handle during its insertion into the wireframe, during the set-up of the implant. This mass may be carved, cut in order to confer to it the desired shape or to reduce its volume which facilitates the set-up of the implant. Thus, the wireframe may present a simple shape which enables its manufacture at a lower cost, for example, by 3D printing. The superimposed two layers can be separated, the textile allows housing the cells in a durable manner and forming a network which is compact and presents a good cohesion.

Advantageously, said textile further includes at least one interlayer disposed between said surface layers, said threads connect said surface layers to said interlayer, said interwoven threads form apertures on said interlayer, preferably, said apertures of said interlayer do not match with said apertures of said opposite faces of said textile and said textile preferably includes connection points between said threads.

The fact that the apertures of the faces do not coincide or coincide only partially, that is to say they are not disposed opposite each other, results in the textile forming a network, a kind of three-dimensional net in which the cells will hook or by which they will be at least retained.

The presence of connection points allows cutting the textile without the latter falling apart or losing its mechanical properties over a large extent.

The interlayer further improves the hooking of the cells and therefore the cohesion of the formed mass. Thus, the sheet forms a network where the cells are housed. When the apertures of the three layers do not coincide or coincide only partially, we obtain a dense network which properly supports the mass formed by the cells; when these will split in the body of the subject, a dense and homogeneous mass is obtained. We also observe, in this case, a more rapid growth of the cells, the formation of a homogeneous mass because the growth of the cells is guided thanks to the textile. Such a textile enables the vascularization and reduces cellular mortality. It enhances the cohesion of the obtained mass, in particular of the fatty mass.

The textile is also a hooking support for cellular elements and growth factors (soluble proteinic elements).

Advantageously, said textile includes pores with dispersed diameters, the arithmetic mean of the diameter of said pores is substantially equal to or smaller than 3.5 and substantially equal to or larger than 1.5 and preferably substantially equal to 2 and in that 75% of said pores have a diameter substantially equal to or larger than 2 and substantially equal to or smaller than 3.5. The diameter of the pores is related in particular to the number of connection points and to their density in the textile. The inventors have noticed that such a pore diameter allows obtaining a good cellular growth and a homogeneous mass which is easy to implant.

Advantageously, said textile has a deformation at break-up in the machine direction and/or in the cross-machine direction lower than 50%. Thus, we obtain a homogeneous mass presenting a good cohesion which makes it easy to handle and to carve, where appropriate.

The textile may be formed by at least two threads of different diameters and the ratio of the diameters of the threads is in particular comprised between 2 and 3. The different diameters allow forming the aforementioned space and easily forming the interlayer, the finer thread being capable of forming a layer without touching the layers above it or beneath it if the clearance between these layers is formed, for example, by the section of the thread with the largest diameter.

The inventors have also set out that good results in terms of cohesion of the tissue mass could be obtained, in particular when said textile has an air permeability higher than or equal to 10000 L/m² and a thickness larger than or equal to 0.50 mm.

According to an embodiment, which may be combined with any one of the aforementioned ones, the device includes a stacking of at least two textile sheets comprising therebetween a layer of cells selected from adipocytes, cells capable of differentiating into adipocytes and mixtures of these two types of cells and said stacking is housed in said wireframe and fills it at least partially and preferably partially. The presence of a void in the wireframe promotes the growth of the cells located between the sheets in the body of the subject. Preferably, the aforementioned cells are obtained through the use of the supernatant after centrifugation of a fatty heap collected on the subject himself; an autologous transplantation actually limiting rejection reactions.

The present invention also concerns a mass adapted to be implanted in the body of a subject in order to replace and/or increase a soft tissue volume.

According to the invention, in a characteristic manner, it comprises at least two superimposed textile sheets, said textile being in particular resorbable, and between said superimposed sheets, cells selected from adipocytes, cells capable of differentiating into adipocytes and mixtures of these two types of cells, said textile is formed by an interweaving of at least two threads, said textile forms a three-dimensional structure which includes at least two superimposed surface layers, forming the opposite two faces of said textile, said threads connect said surface layers, said interwoven threads form pores which pass throughout the thickness of said textile and said textile preferably includes connection points between said threads.

The aforementioned mass may also be used for a direct implantation in the body of the subject, without any wireframe.

Advantageously, said textile further includes at least one interlayer disposed between said surface layers, said threads connect said surface layers to said interlayer, said interwoven threads form apertures on said interlayer, preferably, said apertures of said interlayer do not match with said apertures of said opposite faces of said textile and said textile preferably includes connection points between said threads.

The same advantages and features as those defined with reference to the device apply to the mass of the invention.

Advantageously, the textile includes pores with dispersed diameters, the arithmetic mean of the diameter of said pores is substantially equal to or smaller than 3.5 and substantially equal to or larger than 1.5 and preferably substantially equal to 2 and in that 75% of said pores have a diameter substantially equal to or larger than 2 and substantially equal to or smaller than 3.5.

Advantageously, said textile has a deformation at break-up in the machine direction and/or in the cross-machine direction lower than 50%.

The textile is preferably bioresorbable.

Advantageously, the textile is formed by at least two threads of different diameters and the ratio of the diameters of the threads is in particular comprised between 2 and 3.

Advantageously, the textile has an air permeability higher than or equal to 10000 L/m² and a thickness larger than or equal to 0.50 mm. The obtained advantages are the same as those described with reference to the device of the present invention.

The present invention also concerns a method for manufacturing in vitro an implant adapted to be disposed in the body of a subject for the replacement and/or for the increase of a soft tissue volume.

According to this method, in a characteristic manner,
  we provide a bioresorbable wireframe having a size and a shape determined beforehand;
  we provide at least two sheets of at least one bioresorbable textile formed by an interweaving of at least two threads which form a three-dimensional structure;
  we make at least one first stacking of at least two of said sheets between which we deposit cells selected from adipocytes, cells capable of differentiating into adipocytes and mixtures of these two types of cells, said cells preferably originating from said subject;
  we dispose said first stacking in said wireframe for the implantation of the latter in the body of a subject.

The method according to the invention may be implemented with any embodiment of the wireframe mentioned in the present application.

According to a particular implementation, before or after the insertion of said stacking into said wireframe, we practice an incision in said stacking, in particular parallel to the plane of said sheets, substantially at the level of said lateral openings and in particular above said edge of said wireframe. This incision enables the insertion of the vascular pedicle.

According to a second implementation:
  we make a second stacking of at least two of said sheets between which we deposit cells selected from adipocytes, cells capable of differentiating into adipocytes and mixtures of these two types of cells, said cells preferably originating from said subject;
  we dispose said first and second stackings one on top of the other in said wireframe, so that said transverse passage opens substantially between said first and said second stacking.

In this case, the pedicle is disposed between the two stackings through the transverse passage.

Advantageously, we provide a textile formed by an interweaving of at least two threads, in that said textile forms a three-dimensional structure which includes at least two superimposed surface layers, forming the opposite two faces of said textile, said threads connect said surface layers, said interwoven threads form pores which pass throughout the thickness of said textile and said textile preferably includes connection points between said threads.

The obtained advantages are the same as those aforementioned with reference to the device.

Advantageously, we provide a textile which further includes at least one interlayer disposed between said surface layers, said threads connect said surface layers to said interlayer, said interwoven threads form apertures on said interlayer, preferably, said apertures of said interlayer do not match with said apertures of said opposite faces of said textile and said textile preferably includes connection points between said threads.

Advantageously, said textile includes pores with dispersed diameters, the arithmetic mean of the diameter of said pores is substantially equal to or smaller than 3.5 and substantially equal to or larger than 1.5 and preferably substantially equal to 2 and in that 75% of said pores have a diameter substantially equal to or larger than 2 and substantially equal to or smaller than 3.5.

Preferably, the textile has a deformation at break-up in the machine direction and/or in the cross-machine direction lower than 50%.

Preferably, the textile is formed by at least two threads of different diameters and the ratio of the diameters of the threads is in particular comprised between 2 and 3.

Advantageously, said textile has an air permeability higher than or equal to 10000 L/m² and a thickness larger than or equal to 0.50 mm.

The present invention also concerns a breast implant including the device and/or the mass according to the invention.

Definitions

Throughout the present application, the term «adapted to be implanted in the body of a subject» indicate that all portions of the device which are intended to remain for some time in the body of the subject are made of suited material (s), that is to say of a biocompatible and possibly bioresorbable material.

The terms «soft tissue» refers, in the context of the present invention, to the adipose tissues and more particularly to the deep adipose tissue.

The term «thread» refers to a single yarn or fiber or a group of single yarns or fibers, possibly twisted.

The term «connection point» refers to a node formed by a tight interweaving of a thread on itself or of two threads on each other. A node is such that even if the tension of the threads is zero, the threads do not separate from each other. The term connection point» also refers to any punctual areas for fastening two portions of the same thread or of two portions of two distinct threads on each other or with each other. This may consist, for example, of a punctual area created by bonding or by fusion of the material of the portions of the thread(s).

The term «interweaving» refers to an overlapping of a thread on itself or of two threads on each other; when the tension between two interwoven threads is zero, the interweaving is unraveled.

The term «apertures» refer to voids delimited by at least one thread and formed in a layer by an interweaving of thread(s). The apertures are formed by the spreading of two portions of the same thread or of at least two threads.

The term «pores» refers to voids formed across the thickness of the textile, which pass throughout the thickness of the textile and open onto the two faces of the latter; the pores are formed by the spreading of the interwoven threads.

The term «air permeability» refers to the capacity of the textile to let air flow throughout its fibrous structure.

The term «thickness» refers to the value of the thickness obtained by calculation from the grammage of the textile.

The term «bioresorbable» refers to an object that has the property of being degraded in the body of a living being, the products of degradation being evacuated by said living organism so that said object disappears within a more or less long time which may be roughly determined and which depends on the material of said object.

The term «porosity» represents the ratio void volume/total volume of a textile; the porosity corresponds to the formula $1-\alpha$, where $\alpha$ is the compactness and is calculated according to the measured thickness and the grammage according to the following formula $\alpha = G/\rho d \times Z$ in which G is the measured grammage in $g/m^2$, $\rho f$ the volumetric mass of the material of the threads in $kg/m^3$ and Z the measured thickness in mm.

The term «cells capable of differentiating into adipose cells» refer to the adult stem cells, in particular to the adult mesenchymal cells (originating from an adult individual) which are capable of differentiating into cells capable of differentiating into adipocytes.

The term «machine direction» refers to the direction in which the textile is manufactured.

The term «cross-machine direction» refers to the direction perpendicular to the direction of manufacture of the textile.

The term «elastic modulus» refers to Young's modulus.

FIGURES

The present invention, its features and the various advantages provided thereby will better appear and will be better understood upon reading the following description of three particular embodiments of the present invention, presented as non-limiting illustrative examples with reference to the drawings in which:

FIGS. 1a and 1b schematically represent perspective views of two embodiments of the wireframe of the device of the invention;

FIG. 9 represents a photograph obtained with an optical microscope of a sheet of the textile A (to the top) and of a sheet of the textile B on which a supernatant has been deposited as explained later on;

Figure 1A:
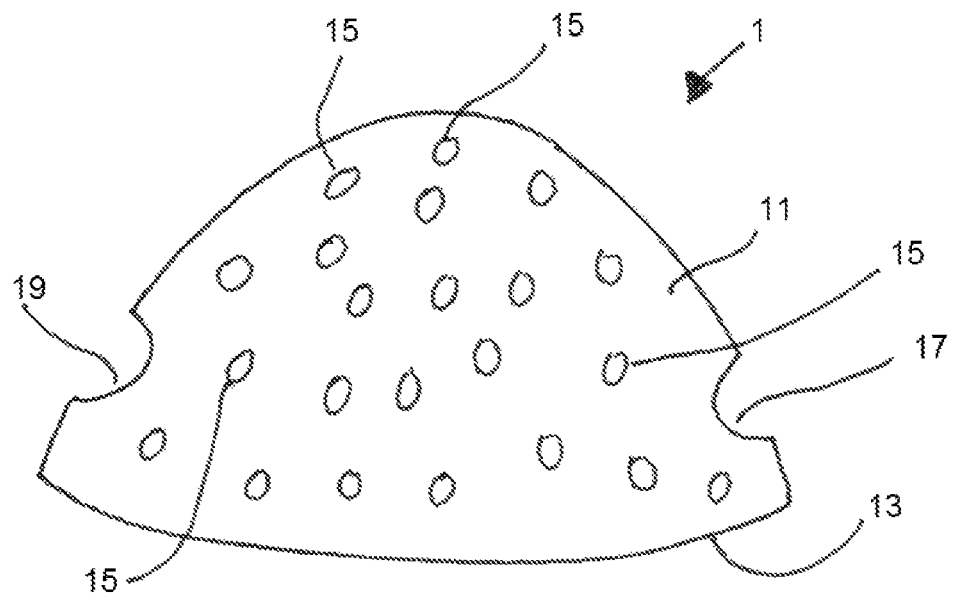

Referring to FIG. 1a, a first embodiment of the wireframe of the device of the invention will be described. The wireframe 1 includes a wall 11 which defines a lower edge 13. The wall 11 includes a plurality of perforations 15 and two lateral openings 17 and 19 which perforate the wall 11 and are located substantially opposite each other so as to define a passage transverse to the wireframe 1. The openings 17 and 19 are located above the lower edge 13.

Figure 1B:
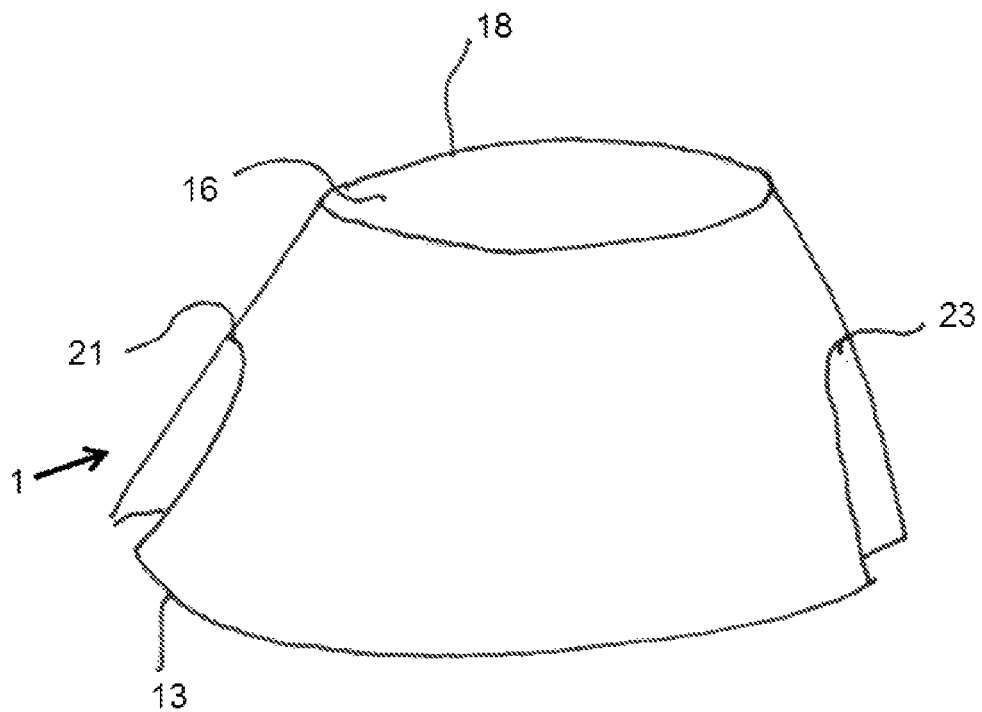

The second embodiment will now be described with reference to FIG. 1b; the elements in common with the first embodiment are referenced identically. The wall 11 of the wireframe includes an open portion 16 located above the open bottom of the wireframe 1. This open portion forms an upper edge 18. The wall also includes two indentations 21 and 23 which cut the lower edge 13 and form openings in the wall 11 above the lower edge 13. These two indentations 21 and 23 form a passage which passes throughout the wireframe 1.

Figure 2:
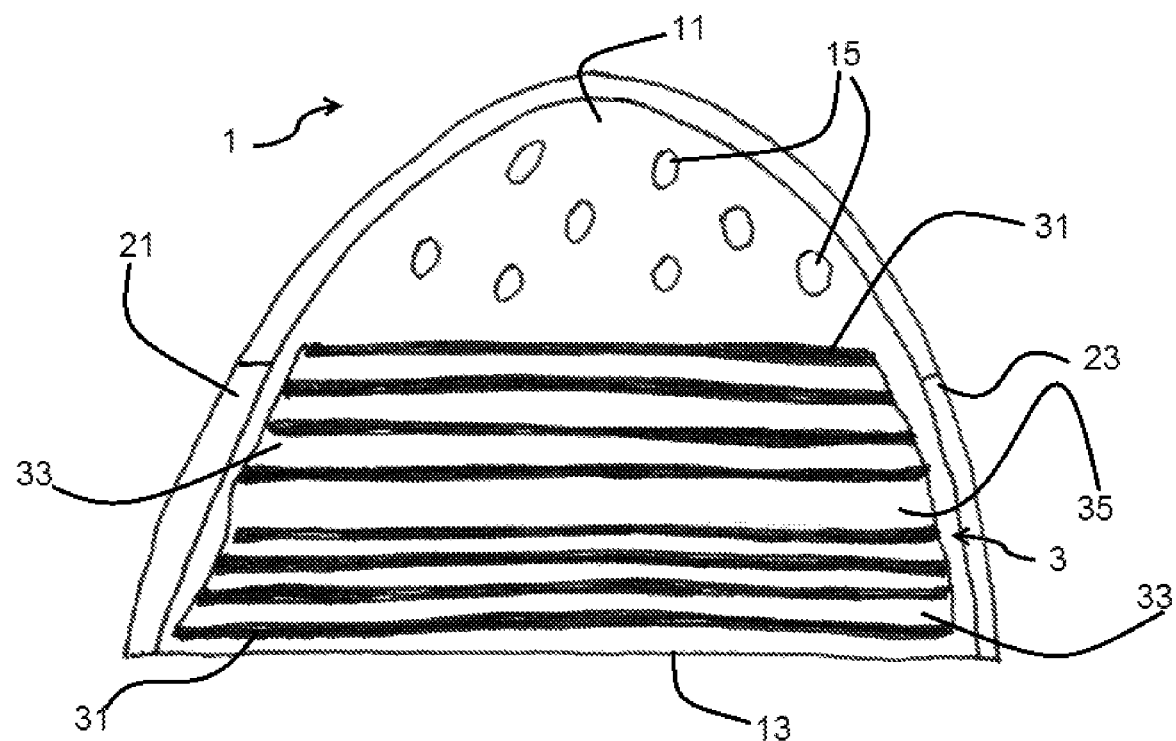
FIG. 2 represents a schematic view of a cross-section of a particular third embodiment of the device of the invention ready for its implantation in the body of a subject.

A third embodiment of the device of the invention will now be described with reference to FIG. 2. The elements in common with the aforementioned two embodiments are referenced identically.

The wireframe 1 includes a wall 11 which has a plurality of perforations 15 and two indentations 21 and 23. The wireframe comprises a stacking 3 which is formed by superimposed textile sheets 31 (in black) and layers of adipocytes 33 (in white) or fatty tissue. The stacking 3 comprises a through passage 35 formed by incision for example. The openings of this passage 35 correspond to the indentations 21 and 23. It is thus possible by introducing a suitable tool through one of the indentations 21 and 23 and by hooking it to a vascular pedicle, to introduce this pedicle into the passage 35 and to deposit it, for example, substantially at the center of the latter.

Figure 10:
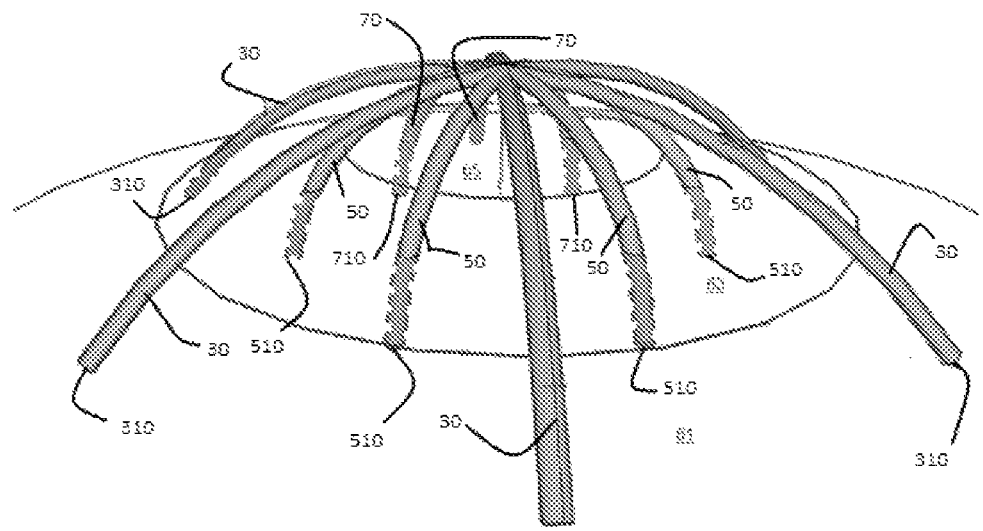
FIG. 10 represents a fourth embodiment of the wireframe of the device of the invention.

A fourth embodiment of the wireframe will now be described with reference to FIG. 10.

In this particular embodiment, the wireframe 1 includes three series of arches 30, 50 and 70. The arches of the first series 30 form 6 feet which correspond to the ends 310 of the arches and which rest on a first textile sheet 61. These arches form a first dome. Inside this dome, lies the second series of arches 50 which includes 6 feet 510 which correspond to the free ends of the arches and which rest on the first sheet 61. The arches of the second series 50 pass throughout a second sheet 63 which is disposed above the first sheet 61. The second sheet 63 has a smaller surface area than the first sheet 61. The arches of the second series 50 pass throughout the second sheet 63 either at the level of its pores, or at the level of openings formed in the latter. The third series of arches 70 is located inside the volume delimited by the arches 5. The arches 70 include 6 feet 710 which correspond to the free ends of the arches 70 and which rest on the first sheet 61. The arches 70 pass throughout a third sheet 65 with a smaller surface area than that of the first and second sheets. Such a wireframe allows defining, with minimum material, a chamber which allows blocking the stacking of the sheets and promotes the cellular growth when cells are deposited on the sheets. Hence, it is easily resorbable in the organism of a subject and allows easy formation of the stacking by simple drilling of the sheets with the arches 30, 50 or 70. The arches naturally define openings which form a through passage enabling the insertion of the pedicle into the three-dimensional structure.

EXAMPLES

Several textiles have been studied with reference to the formation of the stacking which also forms the tissue mass of the invention.

Characterization of the Textiles

Three samples of different textiles, referenced from A to C, have been studied. Each of these textiles has been obtained by interweaving of two threads. All textiles include connection points which in this case consist of nodes. For each of the samples, we have measured the grammage, the thickness, the air permeability and the diameter of the threads. The porosity has been calculated as aforementioned.

The measurement of the grammage (g/m$^2$) has been implemented according to standard ISO 3374. Three samples of each textile sample referenced A to C have been collected with a 14 cm diameter (100 cm$^2$) circular die in order to obtain a good representativeness of the different textiles. Each of the samples is weighted and the grammage is calculated by dividing the measured mass by the surface area of the sample. Afterwards, the average and the standard deviation of the obtained grammages are calculated. All samples whose grammage is not comprised within the range [average−standard deviation; average+standard deviation] are removed and we start again collecting textile samples until obtaining five samples per reference textile comprised within the aforementioned grammage range. The weighing is performed with a Sartorius ENTRIS224i-1S scale.

The air permeability is measured using an AP-36 VVC air permeability meter with a suction pressure drop fixed at 196 Pa according to standard AFNOR G07-111. The air permeability result is expressed in L/m$^2$/s which represents an air flow rate relative to a 1 m$^2$ surface area. The textile samples used for the measurement of permeability have a 20 cm$^2$ surface area.

The measurement of the thickness is carried out according to standard EN ISO 5084 on VVC 2000 apparatus with a used weight corresponding to a 1 kPa load, the unit of measurement is the millimeter. Once the grammage is measured and validated, these same samples are used for the measurement of the thickness of each of the textiles.

The measurement of the diameter of the threads is implemented with an optical microscope. A cross-section of the thread is made using a razor blade and then the diameter of the single yarn(s) forming the thread is observed and measured using a binocular optical microscope (Axiolab Pol of Carl Zeiss).

Table I below groups together the different parameters of each of the textiles.

TABLE I

|  | A | B | C |
| --- | --- | --- | --- |
| Grammage (g/m$^2$) | 84.41 | 129.00 | 108.78 |
| Thickness (mm) | 0.84 | 0.94 | 0.77 |
| Porosity (%) | 91.31 | 88.17 | 87.88 |
| Thread diameter (μm) | 80.07 | 119.52 | 81.75 |
| Air permeability (L/m$^2$/s) | 10960.00 | 9042.00 | 8702.00 |

Moreover, photographs taken with the microscope of each of the samples have also been made. These photographs are shown in FIG. 3A to 3C.

Figure 3A:
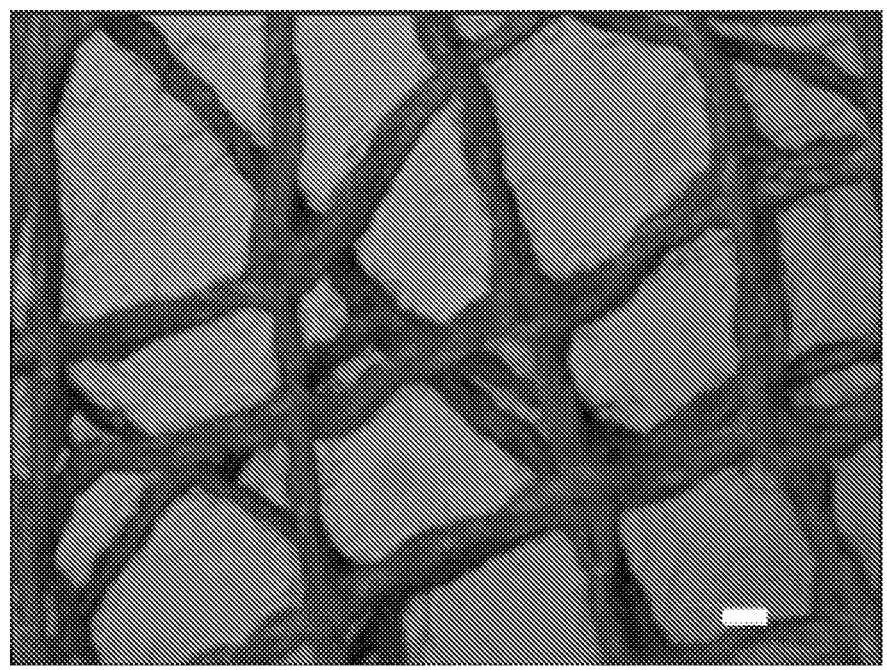
FIG. 3A to 3C represent photographs taken with an optical microscope of the different textiles used for the manufacture of the sheets equipping the device of the invention and referenced from A to C.
Figure 3B:
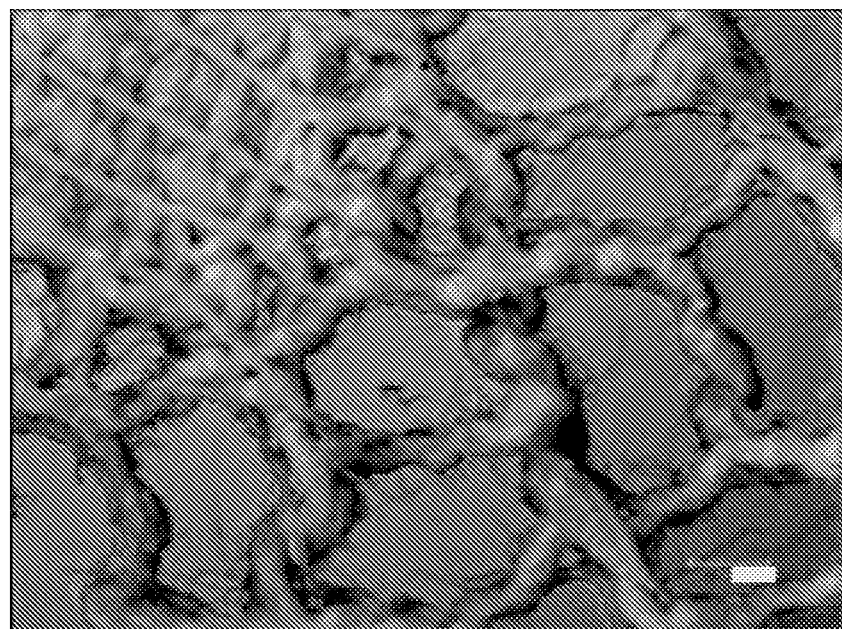
Figure 3C:
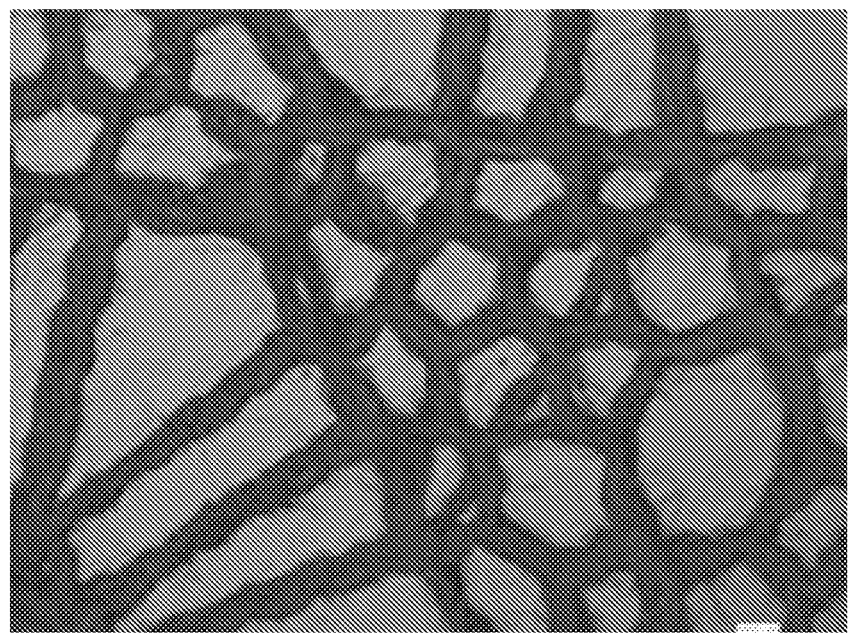

Referring to FIG. 3A to 3C, we notice that Sample A has three superimposed layers of threads, the layers do not mesh into each other. Sample A is obtained by interweaving two threads with different diameters, in this instance a 49 dtx thread with a 120 dtx thread. Sample A includes apertures with different sizes and no compact area formed by side-by-side threads is likely to create an area devoid of apertures. The apertures of one layer do not match with those of the two other ones but the textile includes pores which are formed by the areas where the apertures of the three layers coincide. We also notice that the nodes are sufficiently away from each other so as to enable the layers of threads to locally separate from each other in the direction of the thickness of the textile.

Sample B does not include a thickness formed by an interweaving of two threads of different diameters. Moreover, Sample B has a denser localized area which includes no or only very tiny apertures (see the top left of Photograph B).

Sample C has two layers of threads of different diameters. The size of the apertures is not homogeneous. Sample C is formed by an interweaving of two threads of different diameters. Most of the pores is formed by apertures of the two layers which coincide. The two layers are close to each other because of the large number of nodes; locally it seems that there is only but one single layer of threads (see the area to the left where the pores have a larger size). Sample C includes an area where the interwoven threads form a continuous threads surface without any pores (see the bottom left of FIG. 3C).

Study of the Mechanical Properties of the Textiles

Table II below groups together the results obtained during the tensile tests on the aforementioned textiles A to C.

TABLE II

| Sample | A_machine | A_cross-machine | B | C_machine | C_cross-machine |
|---|---|---|---|---|---|
| Number of considered test pieces | 4/5 | 3/4 | 2/4 | 4/5 | 5/5 |
| Maximum deformation (%) | 32.04 | 57.13 | 67.85 | 53.31 | 91.08 |
| Deformation at break-up (%) | 32.68 | 57.54 | 70.62 | 53.56 | 93.72 |
| Maximum force (N) | 70.53 | 153.67 | 187.60 | 87.53 | 233.58 |
| Force at break-up (N) | 66.65 | 143.20 | 174.50 | 83.60 | 216.98 |
| Maximum stress (Mpa) | 0.71 | 1.54 | 1.88 | 0.88 | 2.34 |
| Elastic modulus (Mpa) | 5.87 | 6.72 | 5.92 | 2.87 | 4.77 |

The term «maximum deformation» refers to the maximum deformation obtained before break-up. The term «machine» indicates a tensile test in the machine direction. In light of the results of Table II, we notice that Sample A, in the machine direction, has the lowest values in terms of deformation, maximum force and force at break-up. Sample A, in the machine direction, is the least extendible of all, with only 32% of deformation at break-up and has an elastic modulus amongst the highest with 5.87 Mpa. Sample A, in the cross-machine direction, extends two times more than in the machine direction with a 57% elongation and has the highest elastic modulus. In general, Sample A is the least extendible of all samples while having the highest elastic modulus.

Sample B presents intermediate mechanical characteristics between the cells of Samples A and C; it is more extendible than Sample A in both directions and less extendible than Sample C in the cross-machine direction. Sample B has an elastic modulus close to that of Sample A with 5.92 Mpa.

Sample C, in the cross-machine direction, is the most extendible with 93% of deformation at break-up and the highest values for the maximum force and the force at break-up but its elastic modulus does not reach the value of that of Sample A with only 4.77 Mpa.

Study of the Size of the Pores of the Samples

We have used a profilometer which allows determining the roughness and the micro-geometry of a surface.

The used profilometer is the AltiSurf 500 supplied by the manufacturer Altimet.

The performed measurements do not follow any standard and are serve only a purely qualitative purpose.

The dimensions of the samples are described in Table III below.

TABLE III

| Sample | A | B | C |
|---|---|---|---|
| Dimensions of the sample (mm × mm) | 50 × 50 | 40 × 40 | 23 × 23 |
| Surface area (mm²) | 2500 | 1600 | 529 |

From the images obtained using the profilometer, the distribution of the size of the pores has been studied thanks to the software ImageJ. This software is an image analysis program developed by the National Institute of Mental Health Bethesda, Md., in the United States. The software allows calculating the surface area as a function of the pixels and of the scale imposed by the user. The images obtained thanks to the profilometer are transformed into 8-bit images, in gray shades. Afterwards, the «Binary» function has been used in order to transform the image in gray shades into an image in black and white. Once this step is completed, we proceed with the delimitation step with the «Threshold» function which allows segmenting the pores and the background. Finally, it is possible to use the «Analyze Particles» function in order to quantify the amount of pores as well as the respective surface area of each of these pores.

It is possible to select the size of the pores that is taken into account in the analysis. All sizes have been taken into account. The pores that are located on the edges of the sample and which are not therefore delimited have not been taken into account, since their size cannot be determined.

For the calculation of the surface area of the pores, we have considered that these pores were circles and then we have calculated the corresponding diameter.

Figure 11:
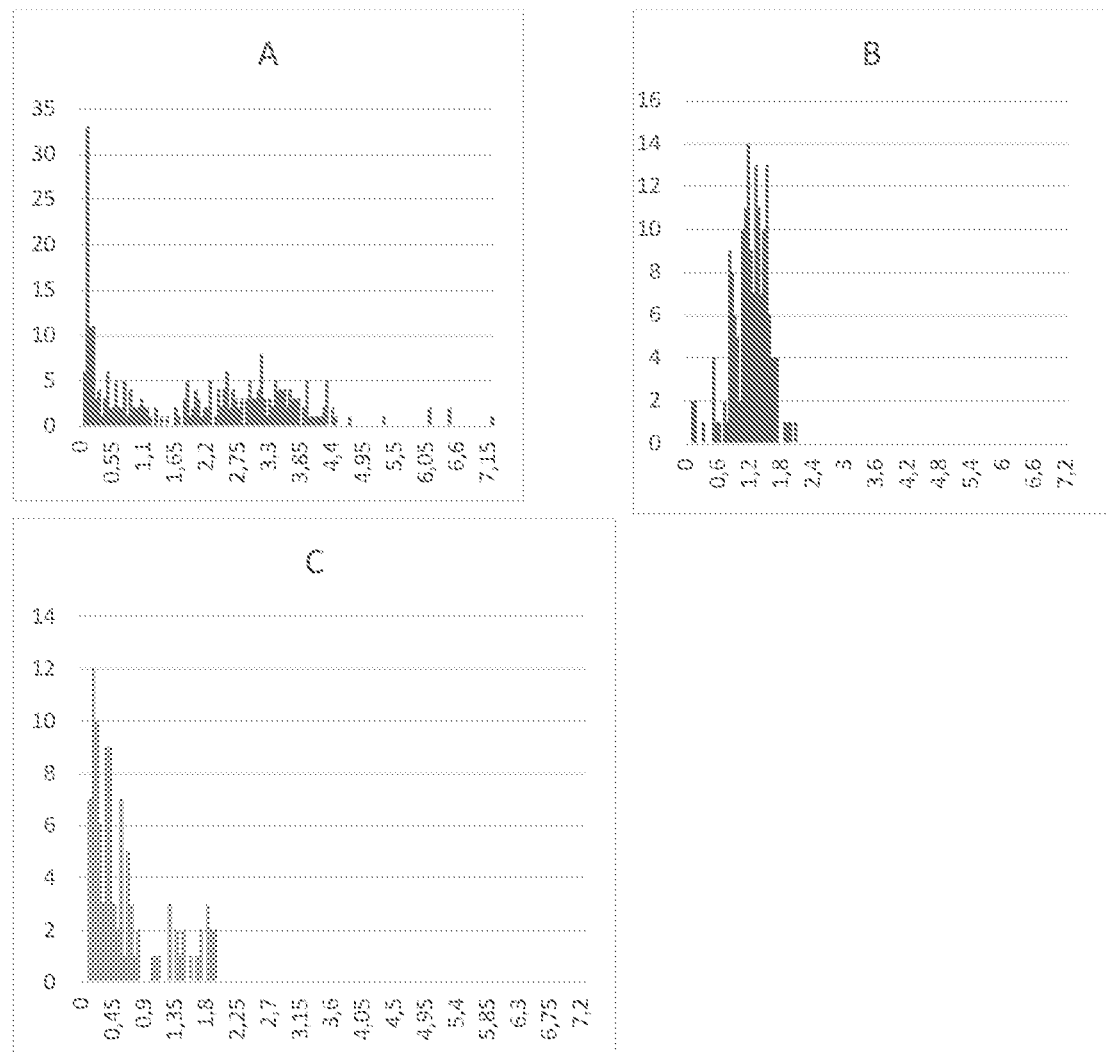
FIG. 11 represents diagrams of the dispersion of the size of the pores for each of Samples A to C.

FIG. 11 represents diagrams of the distribution of the size of the pores. We have considered a 0.05 mm interval in order to have a quite fine distribution.

On the basis of the results represented in FIG. 11, we notice that Sample A has a very heterogeneous distribution of the diameters of pores. This distribution defines the interval on which the samples will be compared. Indeed, the diameters of the pores vary from 0.087 to 7.225 mm. We notice that the small-sized pores are very numerous in comparison with the other samples. For Sample A, there are as many as 33 pores having a diameter comprised between 0.10 and 0.15.

Sample B presents a distribution curve of the size of the pores which is approximately a Gauss curve.

For Sample C, we observe a larger number of small-diameter pores.

Table IV below groups together the different values of the different averages of the sizes of pores for each of the samples.

TABLE IV

| Sample | A | B | C |
|---|---|---|---|
| Arithmetic mean (mm) | 2.002 | 1.211 | 0.629 |
| Geometric mean (mm) | 1.129 | 1.135 | 0.453 |
| Standard deviation (mm) | 1.561 | 0.347 | 0.531 |
| Variance (mm$^2$) | 2.436 | 0.121 | 0.282 |
| Maximum (mm) | 7.225 | 2.071 | 1.939 |
| Minimum (mm) | 0.087 | 0.118 | 0.107 |
| Total number of members | 277 | 171 | 102 |
| Median (mm) | 2.068 | 1.223 | 0.424 |
| Quartile 1 (mm) | 0.407 | 1.021 | 0.242 |
| Quartile 2 (mm) | 2.068 | 1.223 | 0.424 |
| Quartile 3 (mm) | 3.233 | 1.470 | 0.742 |

The difference between the arithmetic and geometric means with reference to Sample A in comparison with the other samples is indicative of the heterogeneity of the distribution of the diameters of the pores. We also observe the highest standard deviation for Sample A among the four samples which shows the large dispersion of the diameters of the pores for Sample A. The standard deviation for Samples B and C being the lowest, it is possible to conclude that the values are centered around the arithmetic mean. Finally, the quartiles indicate the value of the diameter comprising respectively 25, 50 and 75% of the total number of members.

Making of the Tissue Mass

The fatty tissue is prepared following the protocols used for an auto-transplantation. After liposuction, the fatty tissue is centrifuged and we only recover the lipid phase that forms the supernatant, the blood elements remaining in the bottom of the centrifugation tube. The lipid phase contains adipocytes.

We collect several sheets of each of the textiles referenced A to E. We cut 4 cm diameter disks in each of the textiles and we make a stacking of these disks. On one face of each disk, we dispose cells of the aforementioned supernatant with a 25 ml pipette. The supernatant is spread out in order to obtain a constant thickness of adipocytes over each disk. We obtain stackings formed by textile disks spaced by a layer of adipocytes. Afterwards, each stacking is wrapped in a Parafilm M® type film and the set is placed for 24 hours at 37° C. Afterwards, we remove the film and we examine the aspect of the tissue mass thus formed.

Study of the Properties of the Tissue Mass

We have made tissue masses as previously explained with the different textile samples. Afterwards, we have compared some properties of the obtained tissue masses. The following results concern the masses obtained respectively with the textile A and the textile B. The textile C allows obtaining the same results as the textile B.

a) External Aspect of the Tissue Mass

Figure 4:
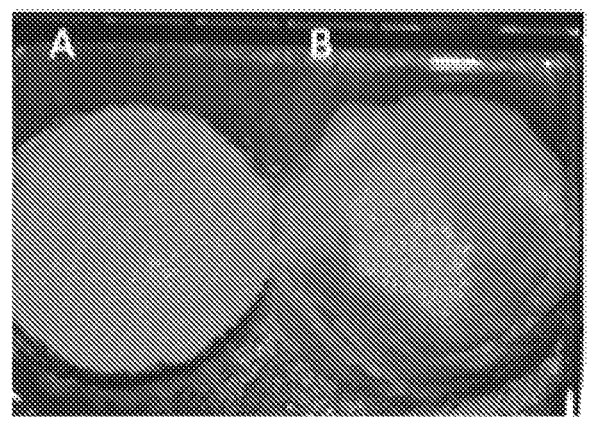
FIG. 4 represents a photograph of the tissue masses obtained respectively with sheets of the textile A, to the left and to the right with sheets of the textile B.

FIG. 4 represents the tissue masses A and B obtained according to the aforementioned protocol, respectively with disks of the textile A and disks of the textile B. In FIG. 4, we notice that the disks of the textile B do not enable holding of the mass when the film is removed. We notice that the mass B presents an expansion of its diameter by about 25% which corresponds to a peripheral collapse of the formed layered structure. On the contrary, the tissue mass A, obtained with the textile A, keeps its shape and does not expand.

b) Cohesion in an Aqueous Medium (Physiologic Serum 9:100 NaCl Water)

Figure 5:
FIG. 5 represents a photograph showing to the left a tissue mass obtained with the textile A in an aqueous solution tube and to the right, a tissue mass obtained with the textile B also plunged in a tube containing an aqueous solution.

We plunge a tissue mass of a smaller size into a physiologic serum (9:100) in order to assess its cohesion. FIG. 5 shows, in the tube to the left, a tissue mass A plunged into water and in the tube to the right, a tissue mass B plunged into water. We notice that the mass A remains in one piece which floats on the surface of water whereas for the mass B, the latter has completely fallen apart and forms a suspension in water.

c) Study of the Cohesion Holding Over Time

Figure 6:
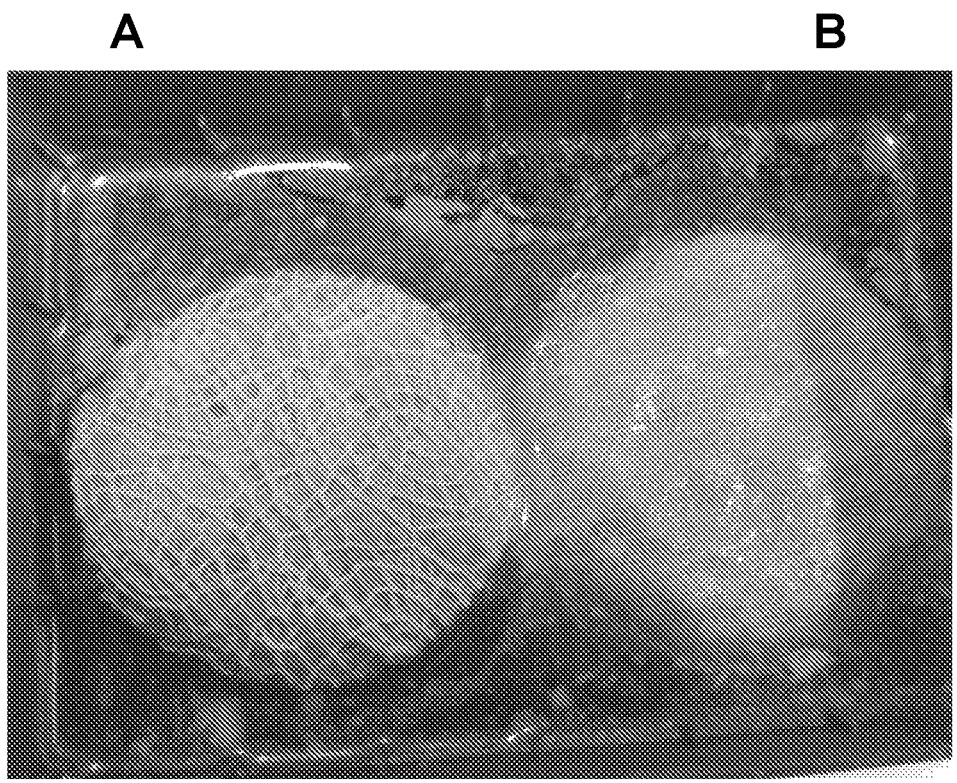
FIG. 6 represents a photograph showing the aspect of the mass obtained with disks of the textile A (to the left) and that of the mass obtained with disks of the textile B (to the right), after 24 h in a physiologic serum.

FIG. 6 represents the aspect of the mass A obtained with disks of the textile A and that of the mass B obtained with disks of the textile B, after 24 h; both masses are placed in a physiologic serum. We notice in FIG. 6, that the mass A remains homogeneous despite the drainage of its surface due to the evaporation of the medium. The mass B falls apart and adipose cells of the supernatant are found in the medium.

d) Dissection of the Tissue Mass

Figure 7:
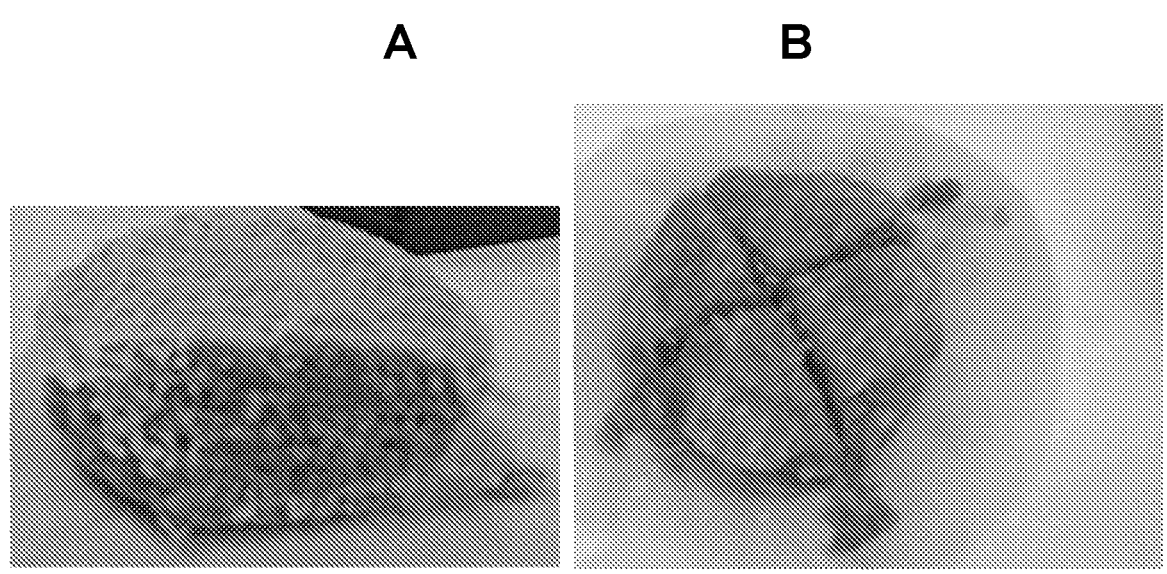
FIG. 7 represents a photograph showing a cross-section of the mass obtained with disks of the textile A, made with the scalpel and, a cross-section of the tissue mass obtained with disks of the textile B.

FIG. 7 shows to the right a cross-section of the mass A made with the scalpel and, to the left, a cross-section of the tissue mass B. We notice that the structure of the mass A is homogeneous which allows obtaining neat slices. The mass B is hardly cut and releases fatty heaps which fall from the tissue mass.

e) Peel-Off Test

Figure 8:
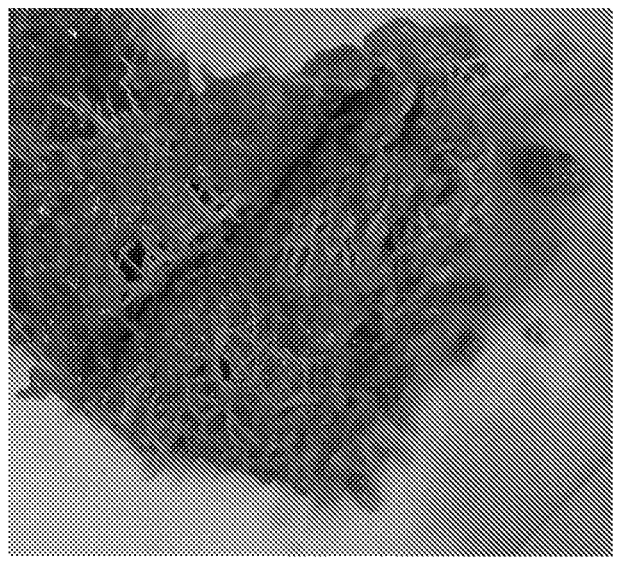
FIG. 8 represents a photograph of the aspect of each of the tissue masses after peel-off of a sheet, the photograph to the top concerns the mass obtained with sheets of the textile A and that to the bottom, the mass obtained with sheets of the textile B.
Figure 8:
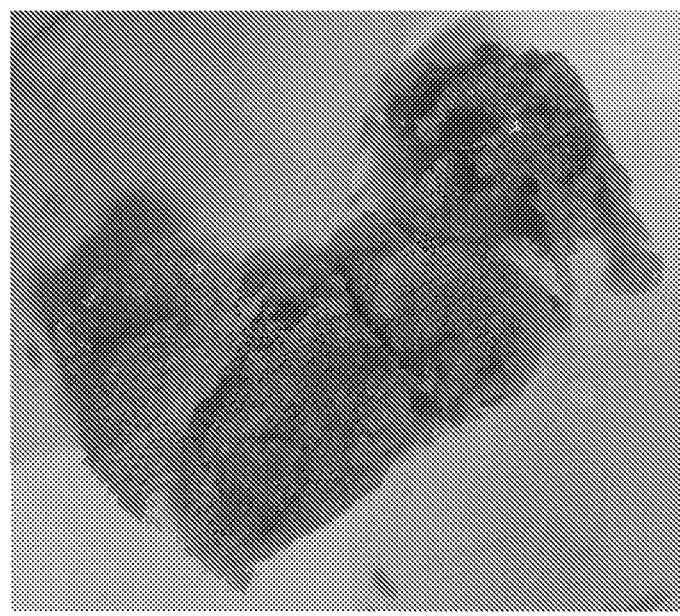

The principle consists in peeling off a disk from each tissue mass A and B and observing whether or not the adipose cells remain on the peeled textile disk. The results are shown in FIG. 8. For the mass A, we observe that the textile disk is completely covered with adipose cells whereas for the mass B, the textile B is easily removed and on cell remains hooked to its surface.

f) Microscopic Observation

Figure 9:
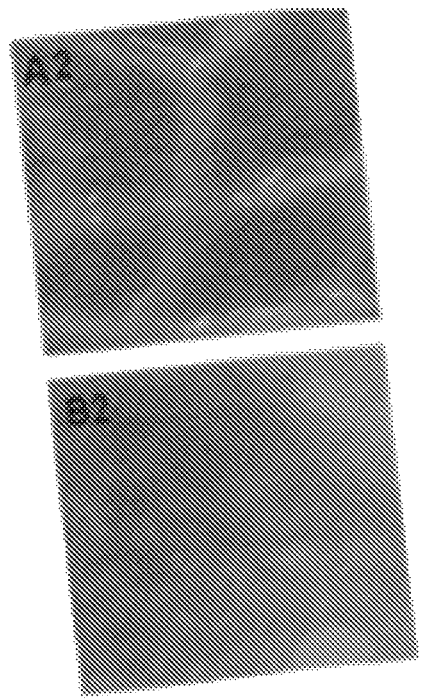

FIG. 9 represents photographs obtained with an optical microscope (indicate the magnification and the type of microscope used) of a sheet of the textile A (to the top) and of a sheet of the textile B on which the aforementioned supernatant has been deposited (for more than 24 hours). We notice that the supernatant spreads out uniformly throughout the entire structure of the textile for the textile A while there are areas devoid of supernatant for the textile B (paler areas, in the bottom right of photograph B2).

The aforementioned results indicate that sheets of the textile A allow obtaining a tissue mass which is homogeneous, compact and which can be cut in order to confer it with a desired shape, for example. This mass being compact, it can also be incised in particular in order to introduce a vascular pedicle therein with neither decohesion nor alteration of the mass.

The invention claimed is:

1. A device adapted to be implanted in the body of a subject to form an implant capable of replacing and/or increasing a soft tissue volume, said device being of the type comprising a three-dimensional wireframe which defines a space internal to said wireframe, wherein said wireframe is bioresorbable, comprises two lateral openings forming a transverse passage enabling the insertion of a vascular pedicle and further comprises at least two sheets of a bioresorbable textile adapted to be stacked one on top of the other in said space internal to said wireframe, and wherein said textile is a three-dimensional structure which includes at least two superimposed surface layers, each layer being a respective face of two opposite faces of said textile, and both layers being formed by an interweaving of at least two same strands connecting and defining said surface layers, said interwoven strands form pores which pass throughout the thickness of said textile; and wherein said textile includes connection points between said surface layers, said connection points corresponding to nodes or fastening areas between said strands, and being distributed so that said surface layers may be separated in the direction of the thickness of the textile over at least 30% of the surface of the textile.

2. The device according to claim 1, wherein said wireframe includes a wall which defines an edge and a plurality of perforations distributed over said wall and/or an open portion formed in said wall and extending above said edge of said wireframe, said open portion extending from the apex of the dome when said wireframe is substantially dome-like shaped.

3. The device according to claim 1, wherein said wireframe includes assembled arches whose free ends are located in the same plane and at least a first group of outer arches and a second group of inner arches, located in the space defined by said outer arches, the free ends of said arches of said first and second groups form feet being located in the same plane, and the feet of the outer arches rest on a first sheet of said at least two sheets of bioresorbable textile, and the feet of the inner arches pass throughout a second sheet of said at least two sheets of bioresorbable textile, said second sheet being disposed above said first sheet.

4. The device according to claim 1, wherein the connection points are distributed so that said surface layers may be separated in the direction of the thickness of the textile over at least 50% of the surface of the textile.

5. The device according to claim 4, wherein said textile further includes at least one interlayer disposed between said surface layers and formed with interwoven threads, said interwoven threads of said surface layer and said interlayer form apertures.

6. The device according to claim 4, wherein said textile includes pores with dispersed diameters, the arithmetic mean of the diameter of said pores is substantially equal to or smaller than 3.5 mm and substantially equal to or larger than 1.5 mm and 75% of said pores have a diameter substantially equal to or larger than 2 mm and substantially equal to or smaller than 3.5 mm.

7. The device according to claim 4, wherein said textile has a deformation at break-up in the machine direction and/or in the cross-machine direction lower than 50%.

8. The device according to claim 4, wherein said textile is formed by at least two threads of different diameters and the ratio of the diameters of the threads is comprised between 2 and 3.

9. The device according to claim 4, wherein said textile has an air permeability higher than or equal to 10000 $L/m^2/s$ and a thickness larger than or equal to 0.50 mm.

10. The device according to claim 1, further comprising a layer of cells selected from adipocytes located between the two textile sheets, the cells being capable of differentiating into adipocytes and mixtures of these two types of cells and said stacking is housed in said wireframe and fills it at least partially.

11. The device according to claim 5, wherein apertures of said interlayer do not match with said apertures of said surface layers of said textile.

12. The device according to claim 4, wherein said textile includes pores with dispersed diameters, the arithmetic mean of the diameter of said pores is substantially equal to 2 mm.

13. A device adapted to be implanted in the body of a subject to form an implant capable of replacing and/or increasing a soft tissue volume, said device being of the type comprising a three-dimensional wireframe which defines a space internal to said wireframe, wherein said wireframe is bioresorbable, comprises two lateral openings forming a transverse passage enabling the insertion of a vascular pedicle and further comprises at least two sheets of a bioresorbable textile adapted to be stacked one on top of the other in said space internal to said wireframe, wherein said wireframe includes assembled arches whose free ends are located in the same plane and at least a first group of outer arches and a second group of inner arches, located in the space defined by said outer arches, the free ends of said arches of said first and second groups form feet being located in the same plane, and the feet of the outer arches rest on a first sheet of said at least two sheets of bioresorbable textile, and the feet of the inner arches pass throughout a second sheet of said at least two sheets of bioresorbable textile, said second sheet being disposed above said first sheet.

* * * * *